(12) United States Patent
Cummins et al.

(10) Patent No.: US 8,192,459 B2
(45) Date of Patent: Jun. 5, 2012

(54) BLOOD VESSEL CLOSURE CLIP AND DELIVERY DEVICE

(75) Inventors: Christy Cummins, Naas (IE); Robert Stevenson, Dublin (IE)

(73) Assignee: Abbott Vascular Inc., Redwood City, CA (US)

( * ) Notice: Subject to any disclaimer, the term of this patent is extended or adjusted under 35 U.S.C. 154(b) by 0 days.

(21) Appl. No.: 12/966,923

(22) Filed: Dec. 13, 2010

(65) Prior Publication Data

US 2011/0144663 A1    Jun. 16, 2011

Related U.S. Application Data

(63) Continuation of application No. 10/517,004, filed as application No. PCT/IE03/00088 on Jun. 4, 2003, now Pat. No. 7,850,709.

(30) Foreign Application Priority Data

Jun. 4, 2002   (IE) .................................. S2002/0451

(51) Int. Cl.
    *A61B 17/08*    (2006.01)
(52) U.S. Cl. ........................................ 606/213; 606/153
(58) Field of Classification Search .................. 606/151, 606/153, 157, 158, 213, 232, 75, 219; 623/1.11, 623/1.36; 227/175.1
    See application file for complete search history.

(56) References Cited

U.S. PATENT DOCUMENTS

| | | |
|---|---|---|
| 287,046 A | 10/1883 | Norton |
| 438,400 A | 10/1890 | Brennen |
| 1,088,393 A | 2/1914 | Backus |
| 1,331,401 A | 2/1920 | Summers |
| 1,596,004 A | 8/1926 | De Bengoa |
| 1,647,958 A | 11/1927 | Ciarlante |
| 1,880,569 A | 10/1932 | Weis |
| 2,087,074 A | 7/1937 | Tucker |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |

(Continued)

FOREIGN PATENT DOCUMENTS

AU    2003297432    7/2004

(Continued)

OTHER PUBLICATIONS

U.S. Appl. No. 12/114,031, May 11, 2011, Office Action.

(Continued)

*Primary Examiner* — Julian Woo
(74) *Attorney, Agent, or Firm* — Workman Nydegger; Randy Shen (57) ABSTRACT

A clip for closing a puncture hole in a blood vessel comprises a ring having a resiliently expandable circumference and a plurality of barbed prongs extending at least approximately in the same direction from one edge of the ring. A device for deploying such a clip is also described.

12 Claims, 5 Drawing Sheets

U.S. PATENT DOCUMENTS

| | | |
|---|---|---|
| 3,482,428 A | 12/1969 | Kapitanov et al. |
| 3,494,533 A | 2/1970 | Green et al. |
| 3,510,923 A | 5/1970 | Blake |
| 3,523,351 A | 8/1970 | Filia |
| 3,586,002 A | 6/1971 | Wood et al. |
| 3,604,425 A | 9/1971 | Le Roy |
| 3,618,447 A | 11/1971 | Goins |
| 3,677,243 A | 7/1972 | Nerz |
| 3,757,629 A | 9/1973 | Schneider |
| 3,805,337 A | 4/1974 | Branstetter |
| 3,823,719 A | 7/1974 | Cummings |
| 3,828,791 A | 8/1974 | Santos |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A | 6/1976 | Murray |
| 3,985,138 A | 10/1976 | Jarvik |
| 4,014,492 A | 3/1977 | Rothfuss |
| 4,018,228 A | 4/1977 | Goosen |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,273,129 A | 6/1981 | Boebel |
| 4,274,415 A | 6/1981 | Kanamoto et al. |
| 4,278,091 A | 7/1981 | Borzone |
| 4,317,445 A | 3/1982 | Robinson |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,396,139 A | 8/1983 | Hall et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Vaillancourt |
| 4,526,174 A | 7/1985 | Froehlich |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,651,737 A | 3/1987 | Deniega |
| 4,664,305 A | 5/1987 | Blake, III et al. |
| 4,665,906 A | 5/1987 | Jervis |
| 4,687,469 A | 8/1987 | Osypka |
| 4,693,249 A | 9/1987 | Schenck et al. |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,147,381 A | 9/1992 | Heimerl et al. |
| 5,156,609 A | 10/1992 | Nakao et al. |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,209,756 A | 5/1993 | Seedhom et al. |
| 5,217,024 A | 6/1993 | Dorsey et al. |
| 5,222,974 A | 6/1993 | Kensey et al. |
| 5,226,908 A | 7/1993 | Yoon |
| 5,236,435 A | 8/1993 | Sewell, Jr. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Janota |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,289,963 A | 3/1994 | McGarry et al. |
| 5,290,243 A | 3/1994 | Chodorow et al. |
| 5,290,310 A | 3/1994 | Makower et al. |

| | | | | | |
|---|---|---|---|---|---|
| 5,292,309 A | 3/1994 | Van Tassel et al. | 5,645,565 A | 7/1997 | Rudd et al. |
| 5,292,332 A | 3/1994 | Lee | 5,645,566 A | 7/1997 | Brenneman et al. |
| 5,304,183 A | 4/1994 | Gourlay et al. | 5,645,567 A | 7/1997 | Crainich |
| 5,304,184 A | 4/1994 | Hathaway et al. | 5,649,959 A | 7/1997 | Hannam et al. |
| 5,304,204 A | 4/1994 | Bregen | D383,539 S | 9/1997 | Croley |
| 5,306,254 A | 4/1994 | Nash et al. | 5,674,231 A | 10/1997 | Green et al. |
| 5,309,927 A | 5/1994 | Welch | 5,676,689 A | 10/1997 | Kensey et al. |
| 5,318,542 A | 6/1994 | Hirsch et al. | 5,676,974 A | 10/1997 | Valdes et al. |
| 5,320,639 A | 6/1994 | Rudnick | 5,681,334 A | 10/1997 | Evans et al. |
| 5,327,908 A | 7/1994 | Gerry | 5,683,405 A | 11/1997 | Yacoubian et al. |
| 5,330,445 A | 7/1994 | Haaga | 5,690,674 A | 11/1997 | Diaz |
| 5,334,216 A | 8/1994 | Vidal et al. | 5,695,504 A | 12/1997 | Gifford, III et al. |
| 5,334,217 A | 8/1994 | Das | 5,695,505 A | 12/1997 | Yoon |
| 5,335,680 A | 8/1994 | Moore | 5,695,524 A | 12/1997 | Kelley et al. |
| 5,340,360 A | 8/1994 | Stefanchik | 5,700,273 A | 12/1997 | Buelna et al. |
| 5,350,399 A | 9/1994 | Erlebacher et al. | 5,716,375 A | 2/1998 | Fowler |
| 5,352,229 A | 10/1994 | Goble et al. | 5,720,755 A | 2/1998 | Dakov |
| 5,364,406 A | 11/1994 | Sewell, Jr. | 5,725,498 A | 3/1998 | Janzen et al. |
| 5,364,408 A | 11/1994 | Gordon | 5,725,552 A | 3/1998 | Kotula et al. |
| 5,366,458 A | 11/1994 | Korthoff et al. | 5,725,554 A | 3/1998 | Simon et al. |
| 5,366,479 A | 11/1994 | McGarry et al. | 5,728,110 A | 3/1998 | Vidal et al. |
| 5,383,896 A | 1/1995 | Gershony et al. | 5,728,114 A | 3/1998 | Evans et al. |
| RE34,866 E | 2/1995 | Kensey et al. | 5,728,122 A | 3/1998 | Leschinsky et al. |
| 5,392,978 A | 2/1995 | Velez et al. | 5,728,132 A | 3/1998 | Van Tassel et al. |
| 5,395,030 A | 3/1995 | Kuramoto et al. | 5,732,872 A | 3/1998 | Bolduc et al. |
| 5,411,520 A | 5/1995 | Nash et al. | 5,735,873 A | 4/1998 | MacLean |
| 5,413,571 A | 5/1995 | Katsaros et al. | 5,752,966 A | 5/1998 | Chang |
| 5,413,584 A | 5/1995 | Schulze | 5,755,726 A | 5/1998 | Pratt et al. |
| 5,416,584 A | 5/1995 | Kay | 5,755,778 A | 5/1998 | Kleshinski |
| 5,417,699 A | 5/1995 | Klein et al. | 5,766,217 A | 6/1998 | Christy |
| 5,419,777 A | 5/1995 | Hofling | 5,766,246 A | 6/1998 | Mulhauser et al. |
| 5,423,857 A | 6/1995 | Rosenman et al. | 5,769,870 A | 6/1998 | Salahieh et al. |
| 5,425,489 A | 6/1995 | Shichman et al. | 5,776,147 A | 7/1998 | Dolendo |
| 5,425,740 A | 6/1995 | Hutchinson, Jr. | 5,779,707 A | 7/1998 | Bertholet et al. |
| 5,431,639 A | 7/1995 | Shaw | 5,782,844 A | 7/1998 | Yoon et al. |
| 5,431,667 A | 7/1995 | Thompson et al. | 5,782,860 A | 7/1998 | Epstein et al. |
| 5,433,721 A | 7/1995 | Hooven et al. | 5,782,861 A | 7/1998 | Cragg et al. |
| 5,437,631 A | 8/1995 | Janzen | 5,795,958 A | 8/1998 | Rao et al. |
| 5,439,479 A | 8/1995 | Shichman et al. | 5,797,928 A | 8/1998 | Kogasaka |
| 5,443,477 A | 8/1995 | Marin et al. | 5,797,931 A | 8/1998 | Bito et al. |
| 5,443,481 A | 8/1995 | Lee | 5,797,933 A | 8/1998 | Snow et al. |
| 5,445,167 A | 8/1995 | Yoon et al. | 5,797,958 A | 8/1998 | Yoon |
| 5,449,359 A | 9/1995 | Groiso | 5,810,776 A | 9/1998 | Bacich et al. |
| 5,456,400 A | 10/1995 | Shichman et al. | 5,810,846 A | 9/1998 | Virnich et al. |
| 5,462,561 A | 10/1995 | Voda | 5,810,851 A | 9/1998 | Yoon |
| 5,464,413 A | 11/1995 | Siska, Jr. et al. | 5,817,113 A | 10/1998 | Gifford, III et al. |
| 5,466,241 A | 11/1995 | Leroy et al. | 5,820,631 A | 10/1998 | Nobles |
| 5,470,010 A | 11/1995 | Rothfuss et al. | 5,827,298 A | 10/1998 | Hart et al. |
| 5,474,557 A | 12/1995 | Mai | 5,830,125 A | 11/1998 | Scribner et al. |
| 5,474,569 A | 12/1995 | Zinreich et al. | 5,833,698 A | 11/1998 | Hinchliffe et al. |
| 5,476,505 A | 12/1995 | Limon | 5,843,167 A | 12/1998 | Dwyer et al. |
| 5,478,352 A | 12/1995 | Fowler | 5,853,421 A | 12/1998 | Leschinsky et al. |
| 5,478,353 A | 12/1995 | Yoon | 5,853,422 A | 12/1998 | Huebsch et al. |
| 5,478,354 A | 12/1995 | Tovey et al. | 5,855,312 A | 1/1999 | Toledano |
| 5,486,195 A | 1/1996 | Myers et al. | 5,858,082 A | 1/1999 | Cruz et al. |
| 5,497,933 A | 3/1996 | DeFonzo et al. | 5,860,991 A | 1/1999 | Klein et al. |
| 5,507,744 A | 4/1996 | Tay et al. | 5,861,005 A | 1/1999 | Kontos |
| 5,507,755 A | 4/1996 | Gresl et al. | 5,868,755 A | 2/1999 | Kanner et al. |
| 5,522,840 A | 6/1996 | Krajicek | 5,868,763 A | 2/1999 | Spence et al. |
| 5,527,322 A | 6/1996 | Klein et al. | 5,871,474 A | 2/1999 | Hermann et al. |
| 5,536,251 A | 7/1996 | Evard et al. | 5,871,501 A | 2/1999 | Leschinsky et al. |
| 5,540,712 A | 7/1996 | Kleshinski et al. | 5,871,525 A | 2/1999 | Edwards et al. |
| 5,540,716 A | 7/1996 | Hlavacek | 5,873,876 A | 2/1999 | Christy |
| 5,544,802 A | 8/1996 | Crainich | 5,879,366 A | 3/1999 | Shaw et al. |
| 5,547,474 A | 8/1996 | Kloeckl et al. | 5,891,088 A | 4/1999 | Thompson et al. |
| 5,560,532 A | 10/1996 | DeFonzo et al. | 5,897,487 A | 4/1999 | Ouchi |
| 5,571,120 A | 11/1996 | Yoon | 5,902,310 A | 5/1999 | Foerster et al. |
| 5,573,784 A | 11/1996 | Badylak et al. | 5,904,697 A | 5/1999 | Gifford, III et al. |
| 5,575,771 A | 11/1996 | Walinsky | 5,906,631 A | 5/1999 | Imran |
| 5,584,879 A | 12/1996 | Reimold et al. | 5,907,893 A | 6/1999 | Zadno-Azizi et al. |
| 5,591,205 A | 1/1997 | Fowler | 5,910,155 A | 6/1999 | Ratcliff et al. |
| 5,593,412 A | 1/1997 | Martinez et al. | 5,919,207 A | 7/1999 | Taheri |
| 5,601,602 A | 2/1997 | Fowler | 5,922,009 A | 7/1999 | Epstein et al. |
| 5,609,597 A | 3/1997 | Lehrer | 5,928,231 A | 7/1999 | Klein et al. |
| 5,613,974 A | 3/1997 | Andreas et al. | 5,928,251 A | 7/1999 | Aranyi et al. |
| 5,618,291 A | 4/1997 | Thompson et al. | 5,935,147 A | 8/1999 | Kensey et al. |
| 5,620,452 A | 4/1997 | Yoon | 5,938,667 A | 8/1999 | Peyser et al. |
| 5,620,461 A | 4/1997 | Muijs Van De Moer et al. | 5,941,890 A | 8/1999 | Voegele et al. |
| 5,643,318 A | 7/1997 | Tsukernik et al. | 5,947,999 A | 9/1999 | Groiso |

| | | | | | | |
|---|---|---|---|---|---|---|
| 5,951,518 | A | 9/1999 | Licata et al. | 6,296,657 | B1 | 10/2001 | Brucker |
| 5,951,576 | A | 9/1999 | Wakabayashi | 6,305,891 | B1 | 10/2001 | Burlingame |
| 5,951,589 | A | 9/1999 | Epstein et al. | 6,319,258 | B1 | 11/2001 | McAllen, III et al. |
| 5,957,936 | A | 9/1999 | Yoon et al. | 6,322,580 | B1 | 11/2001 | Kanner |
| 5,957,938 | A | 9/1999 | Zhu et al. | 6,328,727 | B1 | 12/2001 | Frazier et al. |
| 5,957,940 | A | 9/1999 | Tanner et al. | 6,329,386 | B1 | 12/2001 | Mollison |
| 5,964,782 | A | 10/1999 | Lafontaine et al. | 6,334,865 | B1 | 1/2002 | Redmond et al. |
| 5,976,161 | A | 11/1999 | Kirsch et al. | 6,348,064 | B1 | 2/2002 | Kanner |
| 5,984,934 | A | 11/1999 | Ashby et al. | 6,358,258 | B1 | 3/2002 | Arcia et al. |
| 5,984,949 | A | 11/1999 | Levin | 6,375,671 | B1 | 4/2002 | Kobayashi et al. |
| 5,993,468 | A | 11/1999 | Rygaard | D457,958 | S | 5/2002 | Dycus |
| 5,993,476 | A | 11/1999 | Groiso | 6,383,208 | B1 | 5/2002 | Sancoff et al. |
| 6,001,110 | A | 12/1999 | Adams | 6,391,048 | B1 | 5/2002 | Ginn et al. |
| 6,004,341 | A | 12/1999 | Zhu et al. | 6,395,015 | B1 | 5/2002 | Borst et al. |
| 6,007,563 | A | 12/1999 | Nash et al. | 6,398,752 | B1 | 6/2002 | Sweezer et al. |
| 6,010,517 | A | 1/2000 | Baccaro | 6,402,765 | B1 | 6/2002 | Monassevitch et al. |
| 6,013,084 | A | 1/2000 | Ken et al. | 6,409,739 | B1 | 6/2002 | Nobles et al. |
| 6,015,815 | A | 1/2000 | Mollison | 6,419,669 | B1 | 7/2002 | Frazier et al. |
| 6,019,779 | A | 2/2000 | Thorud et al. | 6,423,054 | B1 | 7/2002 | Ouchi |
| 6,022,372 | A | 2/2000 | Kontos | 6,425,911 | B1 | 7/2002 | Akerfeldt et al. |
| 6,024,750 | A | 2/2000 | Mastri et al. | 6,428,472 | B1 | 8/2002 | Haas |
| 6,030,364 | A | 2/2000 | Durgin et al. | 6,428,548 | B1 | 8/2002 | Durgin et al. |
| 6,030,413 | A | 2/2000 | Lazarus | 6,443,158 | B1 | 9/2002 | Lafontaine et al. |
| 6,033,427 | A | 3/2000 | Lee | 6,443,963 | B1 | 9/2002 | Baldwin et al. |
| 6,036,703 | A | 3/2000 | Evans et al. | 6,447,540 | B1 | 9/2002 | Fontaine et al. |
| 6,036,720 | A | 3/2000 | Abrams et al. | 6,450,391 | B1 | 9/2002 | Kayan et al. |
| 6,045,570 | A | 4/2000 | Epstein et al. | 6,458,130 | B1 | 10/2002 | Frazier et al. |
| 6,048,358 | A | 4/2000 | Barak | 6,461,364 | B1 | 10/2002 | Ginn et al. |
| 6,056,768 | A | 5/2000 | Cates et al. | 6,482,224 | B1 | 11/2002 | Michler et al. |
| 6,056,769 | A | 5/2000 | Epstein et al. | 6,488,692 | B1 | 12/2002 | Spence et al. |
| 6,056,770 | A | 5/2000 | Epstein et al. | 6,500,115 | B2 | 12/2002 | Krattiger et al. |
| 6,059,800 | A | 5/2000 | Hart et al. | 6,506,210 | B1 | 1/2003 | Kanner |
| 6,059,825 | A | 5/2000 | Hobbs et al. | 6,508,828 | B1 | 1/2003 | Akerfeldt et al. |
| 6,063,085 | A | 5/2000 | Tay et al. | 6,517,569 | B2 | 2/2003 | Mikus et al. |
| 6,063,114 | A | 5/2000 | Nash et al. | 6,533,762 | B2 | 3/2003 | Kanner et al. |
| 6,071,300 | A | 6/2000 | Brenneman et al. | 6,533,812 | B2 | 3/2003 | Swanson et al. |
| 6,077,281 | A | 6/2000 | Das | 6,537,288 | B2 | 3/2003 | Vargas et al. |
| 6,077,291 | A | 6/2000 | Das | 6,547,806 | B1 | 4/2003 | Ding |
| 6,080,182 | A | 6/2000 | Shaw et al. | 6,551,319 | B2 | 4/2003 | Lieberman |
| 6,080,183 | A | 6/2000 | Tsugita et al. | 6,569,173 | B1 | 5/2003 | Blatter et al. |
| 6,090,130 | A | 7/2000 | Nash et al. | 6,569,185 | B2 | 5/2003 | Ungs |
| 6,102,271 | A | 8/2000 | Longo et al. | 6,572,629 | B2 | 6/2003 | Kalloo et al. |
| 6,110,184 | A | 8/2000 | Weadock | 6,582,452 | B2 | 6/2003 | Coleman et al. |
| 6,113,612 | A | 9/2000 | Swanson et al. | 6,582,482 | B2 | 6/2003 | Gillman et al. |
| 6,117,125 | A | 9/2000 | Rothbarth et al. | 6,596,012 | B2 | 7/2003 | Akerfeldt et al. |
| 6,117,148 | A | 9/2000 | Ravo | 6,599,303 | B1 | 7/2003 | Peterson et al. |
| 6,117,157 | A | 9/2000 | Tekulve | 6,602,263 | B1 | 8/2003 | Swanson et al. |
| 6,120,524 | A | 9/2000 | Taheri | 6,610,072 | B1 | 8/2003 | Christy et al. |
| 6,126,675 | A | 10/2000 | Shchervinsky et al. | 6,613,059 | B2 | 9/2003 | Schaller et al. |
| 6,136,010 | A | 10/2000 | Modesitt et al. | 6,616,686 | B2 | 9/2003 | Coleman et al. |
| 6,149,660 | A | 11/2000 | Laufer et al. | 6,623,509 | B2 | 9/2003 | Ginn |
| 6,149,667 | A | 11/2000 | Hovland et al. | 6,623,510 | B2 | 9/2003 | Carley et al. |
| 6,152,144 | A | 11/2000 | Lesh et al. | 6,626,918 | B1 | 9/2003 | Ginn et al. |
| 6,152,936 | A | 11/2000 | Christy et al. | 6,626,920 | B2 | 9/2003 | Whayne |
| 6,152,937 | A | 11/2000 | Peterson et al. | 6,632,238 | B2 | 10/2003 | Ginn et al. |
| 6,165,204 | A | 12/2000 | Levinson et al. | 6,634,537 | B2 | 10/2003 | Chen |
| 6,171,277 | B1 | 1/2001 | Ponzi | 6,645,205 | B2 | 11/2003 | Ginn |
| 6,171,329 | B1 | 1/2001 | Shaw et al. | 6,652,538 | B2 | 11/2003 | Kayan et al. |
| 6,179,849 | B1 | 1/2001 | Yencho et al. | 6,652,556 | B1 | 11/2003 | VanTassel et al. |
| 6,193,708 | B1 | 2/2001 | Ken et al. | 6,663,655 | B2 | 12/2003 | Ginn et al. |
| 6,193,734 | B1 | 2/2001 | Bolduc et al. | 6,669,714 | B2 | 12/2003 | Coleman et al. |
| 6,197,042 | B1 | 3/2001 | Ginn et al. | 6,673,083 | B1 | 1/2004 | Kayan et al. |
| 6,198,974 | B1 | 3/2001 | Webster, Jr. | 6,676,671 | B2 | 1/2004 | Robertson et al. |
| 6,200,329 | B1 | 3/2001 | Fung et al. | 6,676,685 | B2 | 1/2004 | Pedros et al. |
| 6,206,895 | B1 | 3/2001 | Levinson | 6,679,904 | B2 | 1/2004 | Gleeson et al. |
| 6,206,913 | B1 | 3/2001 | Yencho et al. | 6,689,147 | B1 | 2/2004 | Koster, Jr. |
| 6,206,931 | B1 | 3/2001 | Cook et al. | 6,695,867 | B2 | 2/2004 | Ginn et al. |
| 6,210,407 | B1 | 4/2001 | Webster | 6,699,256 | B1 | 3/2004 | Logan et al. |
| 6,220,248 | B1 | 4/2001 | Voegele et al. | 6,702,826 | B2 | 3/2004 | Liddicoat et al. |
| 6,221,102 | B1 | 4/2001 | Baker et al. | 6,712,836 | B1 | 3/2004 | Berg et al. |
| 6,245,079 | B1 | 6/2001 | Nobles et al. | 6,712,837 | B2 | 3/2004 | Akerfeldt et al. |
| 6,248,124 | B1 | 6/2001 | Pedros et al. | 6,719,777 | B2 | 4/2004 | Ginn et al. |
| 6,254,617 | B1 | 7/2001 | Spence et al. | 6,726,704 | B1 | 4/2004 | Loshakove et al. |
| 6,254,642 | B1 | 7/2001 | Taylor | 6,743,195 | B2 | 6/2004 | Zucker |
| 6,267,773 | B1 | 7/2001 | Gadberry et al. | 6,743,243 | B1 | 6/2004 | Roy et al. |
| 6,273,903 | B1 | 8/2001 | Wilk | 6,743,259 | B2 | 6/2004 | Ginn |
| 6,277,140 | B2 | 8/2001 | Ginn et al. | 6,749,621 | B2 | 6/2004 | Pantages et al. |
| 6,280,460 | B1 | 8/2001 | Bolduc et al. | 6,749,622 | B2 | 6/2004 | McGuckin et al. |
| 6,287,322 | B1 | 9/2001 | Zhu et al. | 6,755,842 | B2 | 6/2004 | Kanner et al. |

| | | | | | |
|---|---|---|---|---|---|
| 6,767,356 B2 | 7/2004 | Kanner et al. | 2002/0198589 A1 | 12/2002 | Leong |
| 6,780,197 B2 | 8/2004 | Roe et al. | 2003/0004543 A1 | 1/2003 | Gleeson et al. |
| 6,786,915 B2 | 9/2004 | Akerfeldt et al. | 2003/0009180 A1 | 1/2003 | Hinchliffe et al. |
| 6,790,218 B2 | 9/2004 | Jayaraman | 2003/0032981 A1 | 2/2003 | Kanner et al. |
| 6,790,220 B2 | 9/2004 | Morris et al. | 2003/0045893 A1 | 3/2003 | Ginn |
| 6,837,906 B2 | 1/2005 | Ginn | 2003/0055455 A1 | 3/2003 | Yang et al. |
| 6,846,319 B2 | 1/2005 | Ginn et al. | 2003/0065358 A1 | 4/2003 | Frecker et al. |
| 6,860,895 B1 | 3/2005 | Akerfeldt et al. | 2003/0078598 A1 | 4/2003 | Ginn et al. |
| 6,890,343 B2 | 5/2005 | Ginn et al. | 2003/0083679 A1 | 5/2003 | Grudem et al. |
| 6,896,687 B2 | 5/2005 | Dakov | 2003/0093096 A1 | 5/2003 | McGuckin et al. |
| 6,896,692 B2 | 5/2005 | Ginn et al. | 2003/0097140 A1 | 5/2003 | Kanner |
| 6,926,723 B1 | 8/2005 | Mulhauser et al. | 2003/0109890 A1 | 6/2003 | Kanner et al. |
| 6,926,731 B2 | 8/2005 | Coleman et al. | 2003/0125766 A1 | 7/2003 | Ding |
| 6,929,634 B2 | 8/2005 | Dorros et al. | 2003/0144695 A1 | 7/2003 | McGuckin, Jr. et al. |
| 6,942,674 B2 | 9/2005 | Belef et al. | 2003/0158577 A1 | 8/2003 | Pantages et al. |
| 6,942,691 B1 | 9/2005 | Chuter | 2003/0158578 A1 | 8/2003 | Pantages et al. |
| 6,964,668 B2 | 11/2005 | Modesitt et al. | 2003/0195504 A1 | 10/2003 | Tallarida et al. |
| 6,969,397 B2 | 11/2005 | Ginn | 2004/0009205 A1 | 1/2004 | Sawhney |
| 6,989,003 B2 | 1/2006 | Wing et al. | 2004/0059376 A1 | 3/2004 | Breuniger |
| 6,989,016 B2 | 1/2006 | Tallarida et al. | 2004/0068273 A1 | 4/2004 | Fariss et al. |
| 7,001,398 B2 | 2/2006 | Carley et al. | 2004/0073236 A1 | 4/2004 | Carley et al. |
| 7,001,400 B1 | 2/2006 | Modesitt et al. | 2004/0073255 A1 | 4/2004 | Ginn et al. |
| 7,008,435 B2 | 3/2006 | Cummins | 2004/0082906 A1 | 4/2004 | Tallarida et al. |
| 7,008,439 B1 | 3/2006 | Janzen et al. | 2004/0087985 A1 | 5/2004 | Loshakove et al. |
| 7,033,379 B2 | 4/2006 | Peterson | 2004/0092964 A1 | 5/2004 | Modesitt et al. |
| 7,060,084 B1 | 6/2006 | Loshakove et al. | 2004/0092968 A1 | 5/2004 | Caro et al. |
| 7,063,711 B1 | 6/2006 | Loshakove et al. | 2004/0093024 A1 | 5/2004 | Lousararian et al. |
| 7,083,635 B2 | 8/2006 | Ginn | 2004/0093027 A1 | 5/2004 | Fabisiak et al. |
| 7,108,709 B2 | 9/2006 | Cummins | 2004/0097978 A1 | 5/2004 | Modesitt et al. |
| 7,111,768 B2 | 9/2006 | Cummins et al. | 2004/0127940 A1 | 7/2004 | Ginn et al. |
| 7,112,225 B2 | 9/2006 | Ginn | 2004/0143290 A1 | 7/2004 | Brightbill |
| 7,144,411 B2 | 12/2006 | Ginn et al. | 2004/0153122 A1 | 8/2004 | Palermo |
| 7,163,551 B2 | 1/2007 | Anthony et al. | 2004/0158127 A1 | 8/2004 | Okada |
| 7,169,158 B2 | 1/2007 | Sniffin et al. | 2004/0158287 A1 | 8/2004 | Cragg et al. |
| 7,169,164 B2 | 1/2007 | Borillo et al. | 2004/0158309 A1 | 8/2004 | Wachter et al. |
| 7,211,101 B2 | 5/2007 | Carley et al. | 2004/0167511 A1 | 8/2004 | Buehlmann et al. |
| 7,311,720 B2 | 12/2007 | Mueller et al. | 2004/0167570 A1 | 8/2004 | Pantages |
| 7,316,704 B2 | 1/2008 | Bagaoisan et al. | 2004/0191277 A1 | 9/2004 | Sawhney et al. |
| 7,322,995 B2 | 1/2008 | Buckman et al. | 2004/0215232 A1 | 10/2004 | Belhe et al. |
| 7,326,230 B2 | 2/2008 | Ravikumar | 2004/0249412 A1 | 12/2004 | Snow et al. |
| 7,331,979 B2 | 2/2008 | Khosravi et al. | 2004/0254591 A1 | 12/2004 | Kanner et al. |
| 7,335,220 B2 | 2/2008 | Khosravi et al. | 2004/0267193 A1 | 12/2004 | Bagaoisan et al. |
| D566,272 S | 4/2008 | Walberg et al. | 2004/0267308 A1 | 12/2004 | Bagaoisan et al. |
| 7,361,183 B2 | 4/2008 | Ginn | 2004/0267312 A1 | 12/2004 | Kanner et al. |
| 7,361,185 B2 | 4/2008 | O'Malley et al. | 2005/0038460 A1 | 2/2005 | Jayaraman |
| 7,393,363 B2 | 7/2008 | Ginn | 2005/0038500 A1 | 2/2005 | Boylan et al. |
| 7,396,359 B1 | 7/2008 | Derowe et al. | 2005/0059982 A1 | 3/2005 | Zung et al. |
| 7,533,790 B1 | 5/2009 | Knodel et al. | 2005/0075665 A1 | 4/2005 | Brenzel et al. |
| 7,597,706 B2 | 10/2009 | Kanner et al. | 2005/0085851 A1 | 4/2005 | Fiehler et al. |
| D611,144 S | 3/2010 | Reynolds | 2005/0085854 A1 | 4/2005 | Ginn |
| 7,806,904 B2 | 10/2010 | Carley et al. | 2005/0085855 A1 | 4/2005 | Forsberg |
| 7,819,895 B2 | 10/2010 | Ginn et al. | 2005/0090859 A1 | 4/2005 | Ravikumar |
| 7,841,502 B2 | 11/2010 | Walberg et al. | 2005/0119695 A1 | 6/2005 | Carley et al. |
| 7,842,068 B2 | 11/2010 | Ginn | 2005/0121042 A1 | 6/2005 | Belhe et al. |
| 7,850,709 B2 | 12/2010 | Cummins et al. | 2005/0149117 A1 | 7/2005 | Khosravi et al. |
| 7,850,797 B2 | 12/2010 | Carley et al. | 2005/0152949 A1 | 7/2005 | Hotchkiss et al. |
| 7,854,810 B2 | 12/2010 | Carley et al. | 2005/0165357 A1 | 7/2005 | McGuckin et al. |
| 7,857,828 B2 | 12/2010 | Jabba et al. | 2005/0169974 A1 | 8/2005 | Tenerz et al. |
| 7,867,249 B2 | 1/2011 | Palermo et al. | 2005/0177189 A1 | 8/2005 | Ginn et al. |
| 7,879,071 B2 | 2/2011 | Carley et al. | 2005/0187564 A1 | 8/2005 | Jayaraman |
| 7,887,555 B2 | 2/2011 | Carley et al. | 2005/0216057 A1 | 9/2005 | Coleman et al. |
| 7,887,563 B2 | 2/2011 | Cummins et al. | 2005/0222614 A1 | 10/2005 | Ginn et al. |
| 2001/0007077 A1 | 7/2001 | Ginn et al. | 2005/0245876 A1 | 11/2005 | Khosravi et al. |
| 2001/0031972 A1 | 10/2001 | Robertson et al. | 2005/0267528 A1 | 12/2005 | Ginn et al. |
| 2001/0046518 A1 | 11/2001 | Sawhney | 2005/0273136 A1 | 12/2005 | Belef et al. |
| 2001/0047180 A1 | 11/2001 | Grudem et al. | 2005/0273137 A1 | 12/2005 | Ginn |
| 2002/0026215 A1 | 2/2002 | Redmond et al. | 2005/0274768 A1 | 12/2005 | Cummins et al. |
| 2002/0038127 A1 | 3/2002 | Blatter et al. | 2005/0283188 A1 | 12/2005 | Loshakove et al. |
| 2002/0042622 A1 | 4/2002 | Vargas et al. | 2006/0030867 A1 | 2/2006 | Zadno |
| 2002/0049427 A1 | 4/2002 | Wiener et al. | 2006/0034930 A1 | 2/2006 | Khosravi et al. |
| 2002/0058960 A1 | 5/2002 | Hudson et al. | 2006/0047313 A1 | 3/2006 | Khanna et al. |
| 2002/0077657 A1 | 6/2002 | Ginn et al. | 2006/0100664 A1 | 5/2006 | Pai et al. |
| 2002/0082641 A1 | 6/2002 | Ginn et al. | 2006/0167484 A1 | 7/2006 | Carley et al. |
| 2002/0099389 A1 | 7/2002 | Michler et al. | 2006/0190014 A1 | 8/2006 | Ginn et al. |
| 2002/0106409 A1 | 8/2002 | Sawhney et al. | 2006/0190037 A1 | 8/2006 | Carley et al. |
| 2002/0107542 A1 | 8/2002 | Kanner et al. | 2006/0190038 A1 | 8/2006 | Carley et al. |
| 2002/0133193 A1 | 9/2002 | Ginn et al. | 2006/0195123 A1 | 8/2006 | Ginn et al. |
| 2002/0151921 A1 | 10/2002 | Kanner et al. | 2006/0195124 A1 | 8/2006 | Ginn et al. |
| 2002/0183786 A1 | 12/2002 | Girton | 2006/0206146 A1 | 9/2006 | Tenerz |

| | | | | | | |
|---|---|---|---|---|---|---|
| 2006/0253037 | A1 | 11/2006 | Ginn et al. | FR | 2 443 238 | 7/1980 |
| 2006/0253072 | A1 | 11/2006 | Pai et al. | FR | 2 715 290 | 7/1995 |
| 2006/0287674 | A1 | 12/2006 | Ginn et al. | FR | 2 722 975 | 2/1996 |
| 2006/0293698 | A1 | 12/2006 | Douk | FR | 2 768 324 | 3/1999 |
| 2007/0010853 | A1 | 1/2007 | Ginn et al. | GB | 1 358 466 | 7/1974 |
| 2007/0010854 | A1 | 1/2007 | Cummins et al. | GB | 2 075 144 | 11/1981 |
| 2007/0021778 | A1 | 1/2007 | Carly | GB | 2 397 240 | 7/2004 |
| 2007/0060950 | A1 | 3/2007 | Khosravi et al. | IE | S2000/0722 | 10/2001 |
| 2007/0083230 | A1 | 4/2007 | Javois | IE | S2000/0724 | 10/2001 |
| 2007/0112304 | A1 | 5/2007 | Voss | IE | S2001/0547 | 7/2002 |
| 2007/0112365 | A1 | 5/2007 | Hilal et al. | IE | S2001/0815 | 7/2002 |
| 2007/0123817 | A1 | 5/2007 | Khosravi et al. | IE | S2001/0748 | 8/2002 |
| 2007/0179527 | A1 | 8/2007 | Eskuri et al. | IE | S2001/0749 | 8/2002 |
| 2007/0203507 | A1 | 8/2007 | McLaughlin et al. | IE | S2002/0452 | 12/2002 |
| 2007/0225755 | A1 | 9/2007 | Preinitz et al. | IE | S2002/0664 | 2/2003 |
| 2007/0225756 | A1 | 9/2007 | Preinitz et al. | IE | S2002/0665 | 2/2003 |
| 2007/0225757 | A1 | 9/2007 | Preinitz et al. | IE | S2002/0451 | 7/2003 |
| 2007/0225758 | A1 | 9/2007 | Preinitz et al. | IE | S2002/0552 | 7/2003 |
| 2007/0239209 | A1 | 10/2007 | Fallman | IE | S2003/0424 | 12/2003 |
| 2007/0250080 | A1 | 10/2007 | Jones et al. | IE | S2003/0490 | 1/2004 |
| 2007/0265658 | A1 | 11/2007 | Nelson et al. | IE | S2004/0368 | 11/2005 |
| 2007/0270904 | A1 | 11/2007 | Ginn | IE | S2005/0342 | 11/2005 |
| 2007/0276416 | A1 | 11/2007 | Ginn et al. | JP | 58-181006 | 12/1983 |
| 2007/0276488 | A1 | 11/2007 | Wachter et al. | JP | 12 74750 | 11/1989 |
| 2007/0282352 | A1 | 12/2007 | Carley et al. | JP | 2000102546 | 4/2000 |
| 2008/0004636 | A1 | 1/2008 | Walberg et al. | NL | 9302140 | 7/1995 |
| 2008/0004640 | A1 | 1/2008 | Ellingwood | PL | 171425 | 4/1997 |
| 2008/0009794 | A1 | 1/2008 | Bagaoisan et al. | RU | 2086192 | 8/1997 |
| 2008/0058839 | A1 | 3/2008 | Nobles et al. | SU | 495067 | 12/1975 |
| 2008/0065151 | A1 | 3/2008 | Ginn | SU | 912155 | 3/1982 |
| 2008/0065152 | A1 | 3/2008 | Carley | SU | 1243708 | 7/1986 |
| 2008/0086075 | A1 | 4/2008 | Isik et al. | SU | 1324650 | 7/1987 |
| 2008/0093414 | A1 | 4/2008 | Bender et al. | SU | 1405828 | 6/1988 |
| 2008/0114395 | A1 | 5/2008 | Mathisen et al. | SU | 1456109 | 2/1989 |
| 2008/0210737 | A1 | 9/2008 | Ginn et al. | SU | 1560133 | 4/1990 |
| 2008/0221616 | A1 | 9/2008 | Ginn et al. | WO | WO 96/24291 | 8/1996 |
| 2008/0243148 | A1 | 10/2008 | Mikkaichi et al. | WO | WO 97/07741 | 3/1997 |
| 2008/0269801 | A1 | 10/2008 | Coleman et al. | WO | WO 97/20505 | 6/1997 |
| 2008/0269802 | A1 | 10/2008 | Coleman et al. | WO | WO 97/27897 | 8/1997 |
| 2008/0272173 | A1 | 11/2008 | Coleman et al. | WO | WO 98/06346 | 2/1998 |
| 2008/0300628 | A1 | 12/2008 | Ellingwood | WO | WO 98/06448 | 2/1998 |
| 2008/0312666 | A1 | 12/2008 | Ellingwood et al. | WO | WO 98/16161 | 4/1998 |
| 2008/0312686 | A1 | 12/2008 | Ellingwood | WO | WO 98/17179 | 4/1998 |
| 2008/0312740 | A1 | 12/2008 | Wachter et al. | WO | WO 98/18389 | 5/1998 |
| 2008/0319475 | A1 | 12/2008 | Clark | WO | WO 98/24374 | 6/1998 |
| 2009/0112306 | A1 | 4/2009 | Bonsignore et al. | WO | WO 98/25508 | 6/1998 |
| 2009/0137900 | A1 | 5/2009 | Bonner et al. | WO | WO 98/58591 | 12/1998 |
| 2009/0157101 | A1 | 6/2009 | Reyes et al. | WO | WO 99/21491 | 5/1999 |
| 2009/0157102 | A1 | 6/2009 | Reynolds et al. | WO | WO 99/40849 | 8/1999 |
| 2009/0177212 | A1 | 7/2009 | Carley et al. | WO | WO 99/60941 | 12/1999 |
| 2009/0187215 | A1 | 7/2009 | Mackiewicz et al. | WO | WO 99/62408 | 12/1999 |
| 2009/0216267 | A1 | 8/2009 | Willard et al. | WO | WO 99/62415 | 12/1999 |
| 2009/0230168 | A1 | 9/2009 | Coleman et al. | WO | WO 00/06029 | 2/2000 |
| 2009/0287244 | A1 | 11/2009 | Kokish | WO | WO 00/07505 | 2/2000 |
| 2010/0114156 | A1 | 5/2010 | Mehl | WO | WO 00/07640 | 2/2000 |
| 2010/0114159 | A1 | 5/2010 | Roorda et al. | WO | WO 00/27311 | 5/2000 |
| 2010/0160958 | A1 | 6/2010 | Clark | WO | WO 00/27313 | 5/2000 |
| 2010/0168790 | A1 | 7/2010 | Clark | WO | WO 00/56223 | 9/2000 |
| 2010/0179567 | A1 | 7/2010 | Voss et al. | WO | WO 00/56227 | 9/2000 |
| 2010/0179571 | A1 | 7/2010 | Voss | WO | WO 00/56228 | 9/2000 |
| 2010/0179572 | A1 | 7/2010 | Voss et al. | WO | WO 00/71032 | 11/2000 |
| 2010/0179589 | A1 | 7/2010 | Roorda et al. | WO | WO 01/21058 | 3/2001 |
| 2010/0179590 | A1 | 7/2010 | Fortson et al. | WO | WO 01/35832 | 5/2001 |
| 2010/0185234 | A1 | 7/2010 | Fortson et al. | WO | WO 01/47594 | 7/2001 |
| 2010/0217132 | A1 | 8/2010 | Ellingwood et al. | WO | WO 01/49186 | 7/2001 |
| | | | | WO | WO 01/91628 | 12/2001 |

FOREIGN PATENT DOCUMENTS

| | | | | | |
|---|---|---|---|---|---|
| | | | WO | WO 02/19915 | 3/2002 |
| CA | 2 339 060 | 2/2000 | WO | WO 02/19920 | 3/2002 |
| DE | 197 11 288 | 10/1998 | WO | WO 02/19922 | 3/2002 |
| DE | 29723736 U1 | 4/1999 | WO | WO 02/19924 | 3/2002 |
| DE | 19859952 | 2/2000 | WO | WO 02/28286 | 4/2002 |
| DE | 102006056283 | 6/2008 | WO | WO 02/38055 | 5/2002 |
| EP | 0 386 361 | 9/1990 | WO | WO 02/45593 | 6/2002 |
| EP | 0 534 696 | 3/1993 | WO | WO 02/45594 | 6/2002 |
| EP | 0 756 851 | 2/1997 | WO | WO 02/062234 | 8/2002 |
| EP | 0 774 237 | 5/1997 | WO | WO 02/098302 | 12/2002 |
| EP | 0 858 776 | 8/1998 | WO | WO 03/013363 | 2/2003 |
| EP | 0 941 697 | 9/1999 | WO | WO 03/013364 | 2/2003 |
| EP | 1 867 287 | 12/2007 | WO | WO 03/047434 | 6/2003 |

| | | |
|---|---|---|
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 12/143,020, May 11, 2011, Office Action.
U.S. Appl. No. 13/153,594, filed Jun. 6, 2011, Reyes et al.
U.S. Appl. No. 10/667,144, Jun. 6, 2011, Office Action.
U.S. Appl. No. 11/958,281, Mar. 10, 2011, Office Action.
U.S. Appl. No. 11/532,576, Mar. 16, 2011, Issue Notification.
U.S. Appl. No. 10/147,774, Apr. 6, 2011, Issue Notification.
U.S. Appl. No. 13/026,989, Sep. 16, 2011, Office Action.
U.S. Appl. No. 11/675,462, Aug. 3, 2011, Office Action.
U.S. Appl. No. 12/114,031, Aug. 2, 2011, Office Action.
U.S. Appl. No. 10/682,459, Aug. 10, 2011, Issue Notification.
U.S. Appl. No. 10/667,144, Oct. 28, 2011, Notice of Allowance.
U.S. Appl. No. 11/675,462, Dec. 22, 2011, Notice of Allowance.
U.S. Appl. No. 12/393,877, Dec. 13, 2011, Office Action.
U.S. Appl. No. 12/481,377, Jan. 3, 2012, Office Action.
U.S. Appl. No. 12/548,274, Dec. 28, 2011, Restriction Requirement.
U.S. Appl. No. 12/684,470, Dec. 20, 2011, Restriction Requirement.
U.S. Appl. No. 12/684,562, Dec. 28, 2011, Restriction Requirement.
U.S. Appl. No. 12/684,569, Dec. 20, 2011, Restriction Requirement.
U.S. Appl. No. 12/897,358, Jan. 12, 2012, Notice of Allowance.
U.S. Appl. No. 12/941,809, Dec. 13, 2011, Restriction Requirement.
U.S. Appl. No. 12/945,646, Oct. 26, 2011, Office Action.
U.S. Appl. No. 12/955,859, Dec. 15, 2011, Office Action.
U.S. Appl. No. 12/338,977, Jan. 19, 2012, Office Action.
U.S. Appl. No. 12/684,569, Jan. 27, 2012, Office Action.
U.S. Appl. No. 09/610,128, filed Jul. 5, 2000, Kerievsky.
U.S. Appl. No. 09/866,551, filed May 25, 2001, Ginn.
U.S. Appl. No. 12/113,092, filed Apr. 30, 2008, Ginn et al.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 12/897,358, filed Oct. 4, 2010, Carley.
U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/961,331, filed Dec. 6, 2010, Voss.
U.S. Appl. No. 12/945,646, filed Nov. 12, 2010, Carley et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 13/017,636, filed Jan. 31, 2011, Carley et al.
U.S. Appl. No. 13/026,989, filed Feb. 14, 2011, Cummins.
U.S. Appl. No. 13/030,922, filed Feb. 18, 2011, Cummins.
U.S. Appl. No. 13/039,087, filed Mar. 2, 2011, Palermo et al.
U.S. Appl. No. 60/693,531, filed Jun. 24, 2005, Carly.
U.S. Appl. No. 60/696,069, filed Jul. 1, 2005, Pantages et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
"Hand tool for forming telephone connections—comprises pliers with reciprocably driven ram crimping clip around conductors against anvil", Derwent-ACC-No: 1978-B8090A.
Database WPI; Section PQ, Week 200120; Derwent Publications Ltd., London GB; AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PhD, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.

Marshall A.C., Lock J.E., Structural and Compliant Anatomy of the Patent Foramen Ovale in Patients Undergoing Transcatheter Closure, Am Heart J Aug. 2000; 140(2); pp. 303-307.

MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.

MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.

Michael Gianturco, A Play on Catheterization, Forbes, Dec. 1996, p. 146, vol. 158—No. 15.

Inlet Medical Inc. Brochure, pp. 1-2, referencing OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.

P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.

Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.

SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).

Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, vol. 83—No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.

Stretch Comb by Scunci, retrieved via internet at www.scunci.com/productdetail by examiner on Oct. 9, 2007, publication date unavailable.

Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.

SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.

Taber's Cyclopedic Medical Dictionary, 18th Ed. 1997, pp. 747 and 1420.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.

Tomoaki Hinohara, Percutaneous vascular surgery (Prostar® Plus and Techstar® for femoral artery site closure), Interventional Cardiology Newsletter, May-Jul. 1997, pp. 19-22, pp. 24-28, vol. 5—No. 3-4.

UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.

Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

U.S. Appl. No. 09/478,179, Nov. 6, 2000, Notice of Allowance.
U.S. Appl. No. 09/546,998, May 6, 2002, Notice of Allowance.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,813, Jun. 4, 2001, Notice of Allowance.
U.S. Appl. No. 09/933,299, Feb. 26, 2003, Office Action.
U.S. Appl. No. 09/933,299, Jun. 16, 2003, Notice of Allowance.
U.S. Appl. No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.
U.S. Appl. No. 10/081,717, Sep. 29, 2003, Notice of Allowance.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Notice of Allowance.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Office Action.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/147,774, Jun. 8, 2010, Office Action.
U.S. Appl. No. 10/147,774, Dec. 2, 2010, Notice of Allowance.
U.S. Appl. No. 10/240,183, Jul. 27, 2004, Office Action.

U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Office Action.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/264,306, Oct. 29, 2010, Notice of Allowance.
U.S. Appl. No. 10/264,306, Feb. 16, 2011, Issue Notification.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/356,214, Sep. 3, 2010, Notice of Allowance.
U.S. Appl. No. 10/356,214, Feb. 23, 2011, Issue Notification.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Office Action.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/435,104, Oct. 5, 2010, Notice of Allowance.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Mar. 24, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/517,004, Nov. 23, 2010, Issue Notification.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, Aug. 17, 2010, Notice of Allowance.
U.S. Appl. No. 10/541,083, Dec. 1, 2010, Issue Notification.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/616,832, Sep. 20, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/638,115, Aug. 13, 2010, Notice of Allowance.
U.S. Appl. No. 10/638,115, Dec. 22, 2010, Issue Notification.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/667,144, Jun. 22, 2010, Office Action.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/682,459, Oct. 12, 2010, Office Action.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/787,073, Sep. 15, 2010, Issue Notification.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/048,503, Dec. 8, 2010, Issue Notification.
U.S. Appl. No. 11/113,549, Feb. 6, 2007, Office Action.
U.S. Appl. No. 11/113,549, May 30, 2007, Office Action.

U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/113,549, Jan. 4, 2011, Office Action.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/152,562, Sep. 16, 2010, Notice of Allowance.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No. 11/198,811, Oct. 20, 2010, Issue Notification.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/390,586, Jun. 24, 2009, Office Action.
U.S. Appl. No. 11/390,586, Jul. 6, 2010, Office Action.
U.S. Appl. No. 11/396,141, May 22, 2009, Office Action.
U.S. Appl. No. 11/396,141, Aug. 26, 2009, Office Action.
U.S. Appl. No. 11/396,141, May 4, 2010, Office Action.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/406,203, Oct. 6, 2010, Issue Notification.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/427,297, Jan. 30, 2009, Office Action.
U.S. Appl. No. 11/427,297, Sep. 15, 2009, Office Action.
U.S. Appl. No. 11/427,297, Sep. 15, 2010, Office Action.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/427,309, Nov. 15, 2010, Office Action.
U.S. Appl. No. 11/455,993, Feb. 17, 2009, Office Action.
U.S. Appl. No. 11/455,993, Dec. 16, 2009, Office Action.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,576, Mar. 1, 2010, Office Action.
U.S. Appl. No. 11/532,576, Apr. 23, 2010, Office Action.
U.S. Appl. No. 11/532,576, Oct. 13, 2010, Notice of Allowance.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/675,462, Dec. 10, 2009, Office Action.
U.S. Appl. No. 11/675,462, Aug. 31, 2010, Office Action.
U.S. Appl. No. 11/744,089, Nov. 26, 2008, Office Action.
U.S. Appl. No. 11/744,089, Aug. 14, 2009, Office Action.
U.S. Appl. No. 11/757,108, Nov. 25, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/767,818, Sep. 30, 2010, Office Action.
U.S. Appl. No. 11/767,818, Feb. 16, 2011, Office Action.
U.S. Appl. No. 11/852,190, Jun. 24, 2010, Office Action.
U.S. Appl. No. 11/852,190, Nov. 1, 2010, Office Action.
U.S. Appl. No. 11/958,281, Sep. 2, 2010, Office Action.
U.S. Appl. No. 11/958,281, Oct. 8, 2010, Office Action.
U.S. Appl. No. 11/958,295, Aug. 27, 2009, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 11/959,334, Jul. 23, 2010, Notice of Allowance.
U.S. Appl. No. 11/959,334, Nov. 10, 2010, Issue Notification.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,928, Oct. 25, 2010, Office Action.
U.S. Appl. No. 12/106,937, Mar. 30, 2009, Office Action.
U.S. Appl. No. 12/106,937, Nov. 18, 2009, Office Action.
U.S. Appl. No. 12/113,851, Apr. 27, 2010, Office Action.
U.S. Appl. No. 12/113,851, Jun. 24, 2010, Office Action.
U.S. Appl. No. 12/113,851, Dec. 16, 2010, Office Action.
U.S. Appl. No. 12/114,031, Oct. 5, 2010, Office Action.
U.S. Appl. No. 12/114,031, Nov. 22, 2010, Office Action.
U.S. Appl. No. 12/114,091, Oct. 27, 2010, Office Action.
U.S. Appl. No. 12/114,091, Dec. 17, 2010, Office Action.
U.S. Appl. No. 12/402,398, Mar. 9, 2010, Office Action.
U.S. Appl. No. 12/402,398, May 20, 2010, Office Action.
U.S. Appl. No. 12/402,398, Jan. 24, 2011, Office Action.
U.S. Appl. No. 12/403,256, Dec. 16, 2009, Office Action.
U.S. Appl. No. 12/403,256, Mar. 30, 2010, Office Action.
U.S. Appl. No. 12/403,256, Aug. 19, 2010, Notice of Allowance.
U.S. Appl. No. 12/403,256, Nov. 23, 2010, Issue Notification.
U.S. Appl. No. 12/403,277, Jul. 8, 2010, Office Action.
U.S. Appl. No. 12/403,277, Oct. 12, 2010, Office Action.
U.S. Appl. No. 12/945,646, Jan. 20, 2011, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 29/296,370, Feb. 10, 2010, Issue Notification.
U.S. Appl. No. 11/852,190, Mar. 2, 2011, Office Action.
U.S. Appl. No. 12/122,603, Mar. 3, 2011, Office Action.
U.S. Appl. No. 11/396,731, Mar. 22, 2011, Office Action.
U.S. Appl. No. 11/427,297, Mar. 21, 2011, Office Action.
U.S. Appl. No. 10/682,459, Apr. 1, 2011, Notice of Allowance.
U.S. Appl. No. 12/403,277, Mar. 31, 2011, Office Action.
U.S. Appl. No. 12/122,603, Apr. 22, 2011, Office Action.
U.S. Appl. No. 12/113,851, Apr. 27, 2011, Office Action.
U.S. Appl. No. 12/481,377, Apr. 28, 2011, Office Action.
U.S. Appl. No. 13/112,618, filed May 20, 2011, Gianotti et al.
U.S. Appl. No. 13/112,631, filed May 20, 2011, Voss.
U.S. Appl. No. 12/955,859, May 26, 2011, Office Action.
U.S. Appl. No. 12/481,377, Jun. 21, 2011, Office Action.
U.S. Appl. No. 12/114,091, Jul. 7, 2011, Office Action.
U.S. Appl. No. 12/945,646, Jul. 6, 2011, Office Action.
U.S. Appl. No. 12/135,858, Jul. 13, 2011, Office Action.
U.S. Appl. No. 11/396,731, Sep. 1, 2011, Office Action.
U.S. Appl. No. 12/122,603, Sep. 23, 2011, Office Action.
U.S. Appl. No. 12/393,877, Sep. 29, 2011, Office Action.
U.S. Appl. No. 12/955,859, Jul. 21, 2011, Office Action.
U.S. Appl. No. 13/222,899, filed Aug. 31, 2011, Carley et al.
U.S. Appl. No. 12/897,358, Aug. 22, 2011, Office Action.
U.S. Appl. No. 11/767,818, Feb. 3, 2012, Notice of Allowance.
U.S. Appl. No. 12/684,542, Jan. 30, 2012, Restriction Requirement.
U.S. Appl. No. 12/113,851 mailed Mar. 29, 2012 Office Action.
U.S. Appl. No. 12/114,091 mailed Apr. 5, 2012 Office Action.
U.S. Appl. No. 12/688,065 mailed Mar. 13, 2012 Office Action.
U.S. Appl. No. 12/987,792 mailed Mar. 13, 2012 Office Action.

BLOOD VESSEL CLOSURE CLIP AND DELIVERY DEVICE

CROSS-REFERENCE TO RELATED APPLICATIONS

The present application is a continuation of U.S. patent application Ser. No. 10/517,004, entitled "Blood Vessel Closure Clip and Delivery Device," and filed Jun. 6, 2005, now U.S. Pat. No. 7,850,709, which is a United States nationalization of International Application No. PCT/IE2003/00088 filed Jun. 4, 2003, which claims priority to Irish Patent Application No. 2002/0451, entitled "Blood Vessel Closure Clip and Delivery Device", and filed Jun. 4, 2002. The preceding applications are each incorporated herein by reference in their entirety.

FIELD OF THE INVENTION

This invention relates to a clip for closing a puncture hole in a blood vessel, and to a device for closing a puncture hole using such a clip.

BACKGROUND OF THE INVENTION

Numerous medical diagnostic and interventional procedures involve the use of long catheters, which are placed within the human vascular system. These catheters are delivered over guide wires to positions in the heart for cardiac procedures and into the brain for neurological procedures. The point of entry is normally a puncture hole in the femoral artery in the patient's groin. Once the procedure has been completed the catheter and guide wire are removed and the puncture hole must be closed in order to prevent excessive bleeding and the possibility of infection. Traditionally this puncture hole has been closed by maintaining manual pressure at the puncture site until homeostasis occurs around the puncture hole or placing sand bags on an area of the groin close to the puncture hole and keeping the patient immobilized until homeostasis occurs.

In recent times, a number of medical devices have been developed and marketed for the purpose of closing this puncture hole. These devices fall broadly into two categories (a) mechanical closure devices such as those which use sutures or staples to mechanically close the puncture hole, and (b) occlusion devices such as collagen plugs and gels. Examples of prior art in this area include U.S. Pat. Nos. 5,860,991 and 6,322,580.

U.S. Pat. No. 5,860,991 describes a device for closing puncture holes utilizing a suture. The device is positioned into the artery over the guide wire until a blood signal appears at the proximal end indicating proper position has been attained. At this point, an internal anchor is deployed and needles are advanced from outside the artery, through the arterial wall and into the anchor component to grab opposite ends of a suture loop. The needles are then retracted back into the device and the device is removed from the artery leaving the open ends of the suture external on the patient's skin. A knot is tied and run down the suture tightening the loop around the puncture hole and closing it. A cutter device is then used to cut the suture.

The problems associated with this device are the significant number of steps in its use, tying of the suture loop involves a sawing action around the puncture hole which could unintentionally cause the suture to cut its way through the hole, pushing needles from outside the artery to inside creates two additional puncture holes and finally a loop of suture remains inside the artery and has the potential to dislodge plaque within the artery.

Another example of a mechanical closure device is described in U.S. Pat. No. 6,322,580, which uses a metallic staple to close the puncture hole. This device involves the use of a special dilator and sheath, which are guided into the femoral artery over a guide wire. Once the guide wire is removed, internal stabilizers are activated and refracted against the internal wall of the artery. The sheath dilator is then removed and a stapler device is advanced through the sheath and the staple deployed into the arterial wall. The stapler is then removed, the stabilizers deactivated and the introducer sheath removed from the tissue tract.

Problems associated with this device include the use of a specialized sheath, which must be inserted over the guide wire and advanced into the tissue tract before the closure procedure can take place. In addition delicate stabilizer type devices must be deployed within the artery before the stapler can be delivered to close the puncture hole. Once the staple is delivered, the staple device is removed from the sheath, the internal stabilizers are then collapsed and retracted through the puncture hole and into the sheath before the sheath itself can be removed from the tissue tract.

While both devices described above are effective in terms of closing puncture holes they are mechanically complex in nature in terms of operation. In addition, a significant number of steps are involved in the procedure. The end users of such devices are more familiar with catheter-based technologies delivered over guide wires, combined with the inflation and deflation of balloons. Therefore, there is a need for an improved puncture closure device which operates in a manner more consistent with catheter based devices such as angiography and angioplasty catheters. In addition, there is a need to reduce the complexity of such devices by reducing the number of components involved and the number of steps involved in the procedure.

BRIEF SUMMARY

Accordingly, the present invention provides a clip for closing a puncture hole in a blood vessel, the clip comprising a ring having a resiliently expandable circumference and a plurality of barbed prongs extending at least approximately in the same direction from one edge of the ring.

The ring may be circular or any suitable closed-loop shape.

The invention further provides a device for closing a puncture hole in a blood vessel using a clip of the kind aforesaid, the apparatus comprising an elongated body having a front end for insertion through the hole into the blood vessel and a clip expander positioned on the body rearwardly of the front end for receiving the clip with its ring surrounding the expander and its prongs projecting towards the front end of the body, the clip expander being actuable to resiliently expand the circumference of the ring, the clip being movable forwardly in its expanded state so that the prongs pierce the tissue around the hole, and the clip expander thereafter being actuable to release the clip so that the body and clip expander can be withdrawn from the ring.

In one embodiment, the clip, herein referred to as a "ring occluder", is placed over a deflated balloon which in turn is bonded to the shaft of a plastic catheter. Inflation of the balloon exerts an outward expanding force under the ring occluder causing it to expand to a diameter equivalent to a fully expanded diameter of the balloon on which it sits. Barbed legs extend from one edge of the occluder ring for a distance of 3-5 mm. The catheter has three lumens, one provides a channel for liquid to inflate the balloon, one is a channel for blood and the third channel accommodates the guide wire.

In clinical use, the catheter is positioned on the guide wire and delivered over the guide wire through the tissue tract and into the blood vessel. The catheter is advanced until a blood signal appears at the bleed back port. This indicates that the blood entry port is now positioned within the blood vessel. The catheter is now refracted until blood flow stops indicating that the blood entry port is now positioned within the puncture hole and the ring occluder is positioned a pre-determined distance form the wall of the blood vessel. The guide wire may now be removed. The balloon is then inflated using saline solution which in turn causes the ring occluder to increase in diameter and expand outward into the tissue tract. The diameter of the balloon on the rear side of the ring occluder is greater in diameter so as to provide a shoulder or edge to advance the ring occluder forward. Once fully expanded the catheter is pushed forward causing the barbed legs of the ring occluder to penetrate the surrounding tissue and arterial wall in the proximity of the puncture hole. The catheter continues to advance until significant forward resistance is met. This indicates to the user that the catheter should not be advanced any further as the barbed legs should now be positioned within the arterial wall. The expanding balloon is then deflated, the guide wire removed from the catheter and the catheter removed from the tissue tract. On removal of the catheter, the recoiling force of the ring occluder will pull the edges of the puncture hole together thereby sealing the hole closed.

In another embodiment, the balloon is replaced by a sliding collar which has splines which are forced mutually outwards to deform the ring occluder.

The advantage of such devices are that they are significantly simpler to operate than previously described mechanical closure devices. In addition, the mode of operation of the balloon device is consistent with that of other devices used by interventional radiologists and cardiologists in that it provides a catheter delivered over a guide wire with a balloon which is inflated from an external port.

BRIEF DESCRIPTION OF THE DRAWINGS

Embodiments on the invention will now be described, by way of example, with reference to the accompanying drawings, in which.

DETAILED DESCRIPTION

Figure 1:
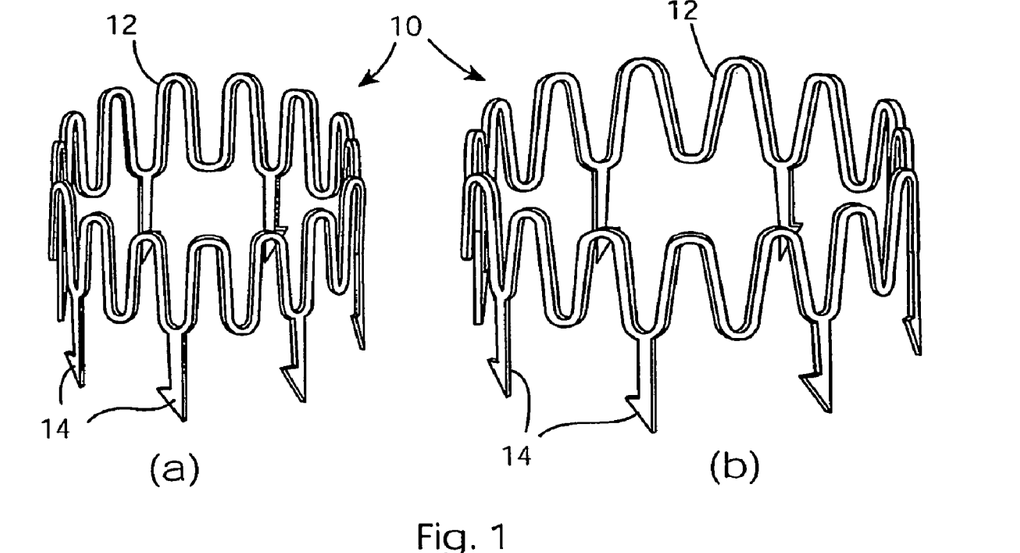
FIG. 1 is a perspective view of one embodiment of a ring occluder according to the invention in both its unexpanded and expanded conditions.

Referring first to FIG. 1, a ring occluder 10 for closing a puncture hole in a blood vessel comprises a circumferentially continuous metal ring 12. The circumference of the ring 12 is sinuous and the ring has a plurality of sharp metal prongs 14 extending at least approximately in the same direction from one edge (in FIG. 1 the lower edge) of the ring 12. The prongs are 3-5 mm in length and extend from alternate minima of the sinuous shape. The prongs 14 are barbed, meaning in the present context that they are configured to resist withdrawal once they penetrate tissue. The prongs 14 preferably mutually converge slightly towards the centre axis of the ring 12. FIG. 1(a) shows the ring occluder in its non-expanded state, while FIG. 1(b) shows the ring occluder in its expanded state where the pitch between the peaks of the sinuous configuration have been increased in a manner which provides uniform expansion of the ring at all points on its circumference. The pitch between the barbed prongs increases accordingly.

Figure 2:
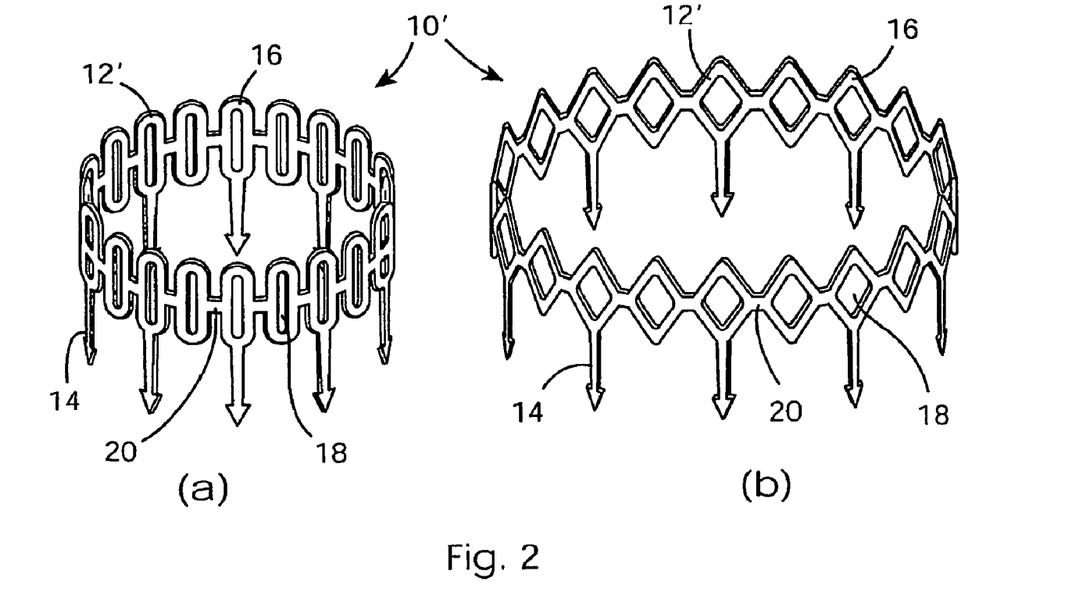
FIG. 2 is a perspective view of a second embodiment of a ring occluder in its unexpanded and expanded conditions.

FIG. 2(a) shows an alternative embodiment of ring occluder 10' in its non-expanded state. In this case, the circumference of the ring 12' is made up of a plurality of oval-shaped segments 16 each with a longitudinal central slit 18. The oval segments 16 are disposed side-by-side round the ring 12 with their longitudinal axes substantially parallel. Each oval segment 16 is joined to the next by a narrow central waist 20. On expansion of the ring as illustrated in FIG. 2(b) the oval segments expand to a more round or open configuration therefore increasing the overall diameter of the ring 12 and the pitch between the barbed legs 14 which extend from the base of every second oval segment.

In both cases, the material used to fabricate the ring occluders 10 and 10' is such that permanent metal deformation does not occur on expansion of the occluder from its non-expanded state to its expanded state. The force exerted on the occluders is such that they remain within the elastic range of the material used thereby ensuring that when the expanding force is removed the occluder returns resiliently to its non-expanded state. Preferably, the diameter of the ring 12 can be resiliently increased by a factor of three with return substantially to its original diameter upon removal of the expanding force. An example of a suitable material for making the occluder is Nitinol or Memory Metal.

Figure 3:
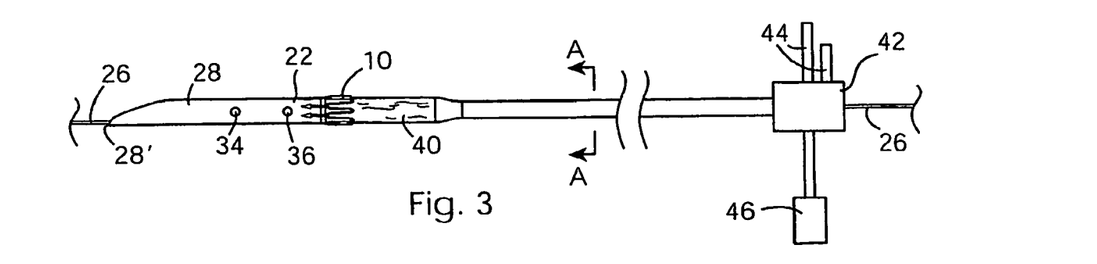
FIG. 3 is a plan view of a first embodiment of catheter delivery device for the ring occluder of FIG. 1 or FIG. 2.
Figure 4:
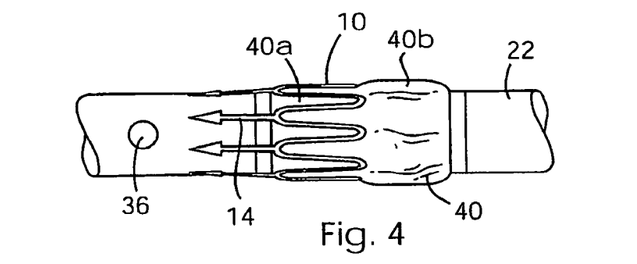
FIG. 4 is an enlarged view of the delivery device of FIG. 3 in the region of the ring occluder and inflatable balloon.
Figure 5:
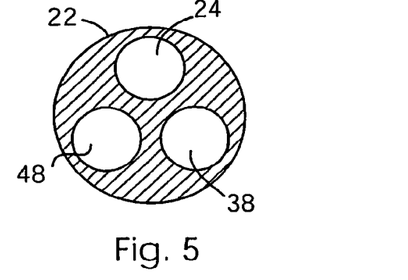
FIG. 5 is a cross sectional view of the catheter on the plane A-A of FIG. 3.

FIGS. 3 to 5 show a first embodiment of catheter delivery device with a ring occluder 10 in position (the device could just as well be used with the ring occluder 10'). The catheter 22 is a flexible, elongated plastics body having a longitudinal bore 24 (FIG. 5) by which the catheter can be slid along a pre-positioned guide wire 26. The front end 28 of the catheter 22 is tapered down onto the guide wire 26 which guides it into position within the blood vessel 30, FIG. 6, through a hole 32 in the sidewall of the blood vessel. Between the front end 28 and the ring occluder 10 is a blood entry port 34. The port 34 allows blood to enter a further longitudinal bore 38 in the catheter 22. An inflatable enclosure ("balloon") 40 is positioned on the catheter 22 approximately 5 cm to the rear of the extreme forward tip 28' of the front end 28. The balloon 40 coaxially surrounds the catheter and in its deflated state lies tightly against the catheter body. The ring occluder 10 is positioned on the balloon 40 toward its forward end, the ring 12 coaxially surrounding the balloon and catheter. A hub 42 is positioned at the rear end of the catheter 22 from which extends a blood port 44 connected to bore 38 within the catheter, which in turn is connected to blood entry port 34. In addition, there is a balloon inflation port 46 connected to a further longitudinal bore 48 in the catheter 22, the bore 48 communicating with the interior of the balloon 40. The port 46 allows fluid under pressure (such as a saline solution) to be delivered into the balloon 40 to inflate it, and also allows fluid in the balloon to be vented to allow it to revert to its deflated state.

FIG. 4 is a view of the device in the region of the ring occluder 10. The balloon 40 is formed with two axially adjacent regions 40a, 40b such that when the balloon is inflated these regions have different diameters, FIG. 7. In particular, when the balloon is inflated the front region 40a, around which the occluder 10 is positioned, has a lesser diameter than the adjacent rear region 40b. The reason for this is to provide a shoulder 40c behind the ring 12 with which the ring occluder 10 can be pushed forward into the tissue surrounding the puncture hole 32 by pushing the catheter 22 as a whole in a forward direction. Only the ring 22 is positioned on the balloon 40. The barbed prongs 14 extend freely in a forward direction and converge slightly towards the catheter body. In order to ensure that, when the balloon is inflated, the region 40b does not expand at the expense of the region 40a, the region 40b and shoulder 40c are made of a thicker material than the region 40a.

Figure 6:
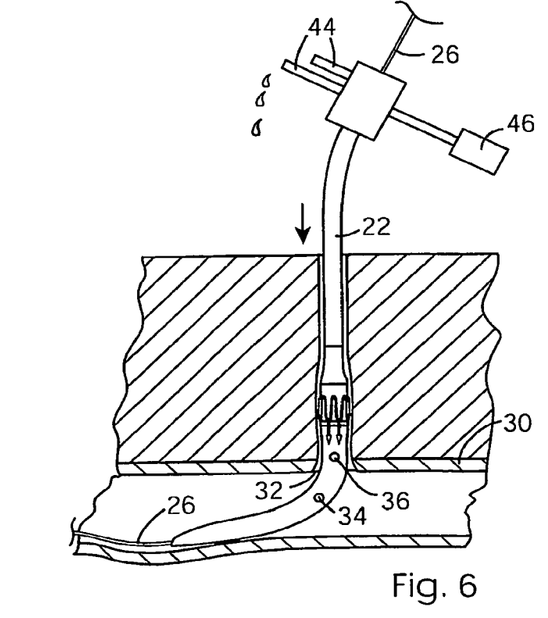
FIGS. 6-10 illustrate successive stages of the catheter delivery device in use.
Figure 7:
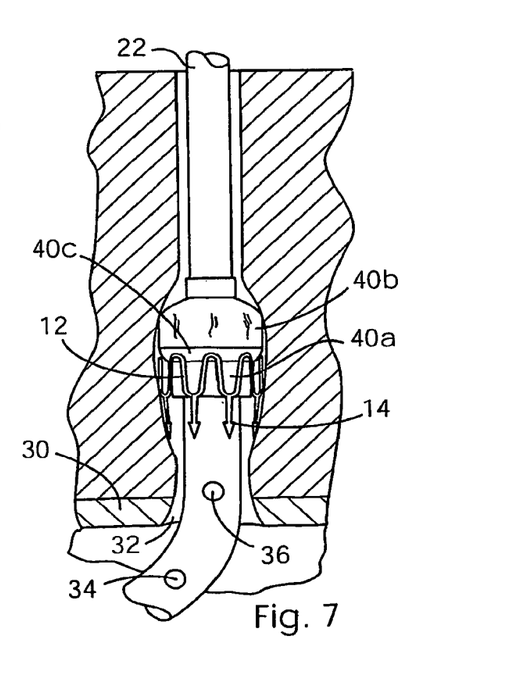
Figures 8, 9, 10:
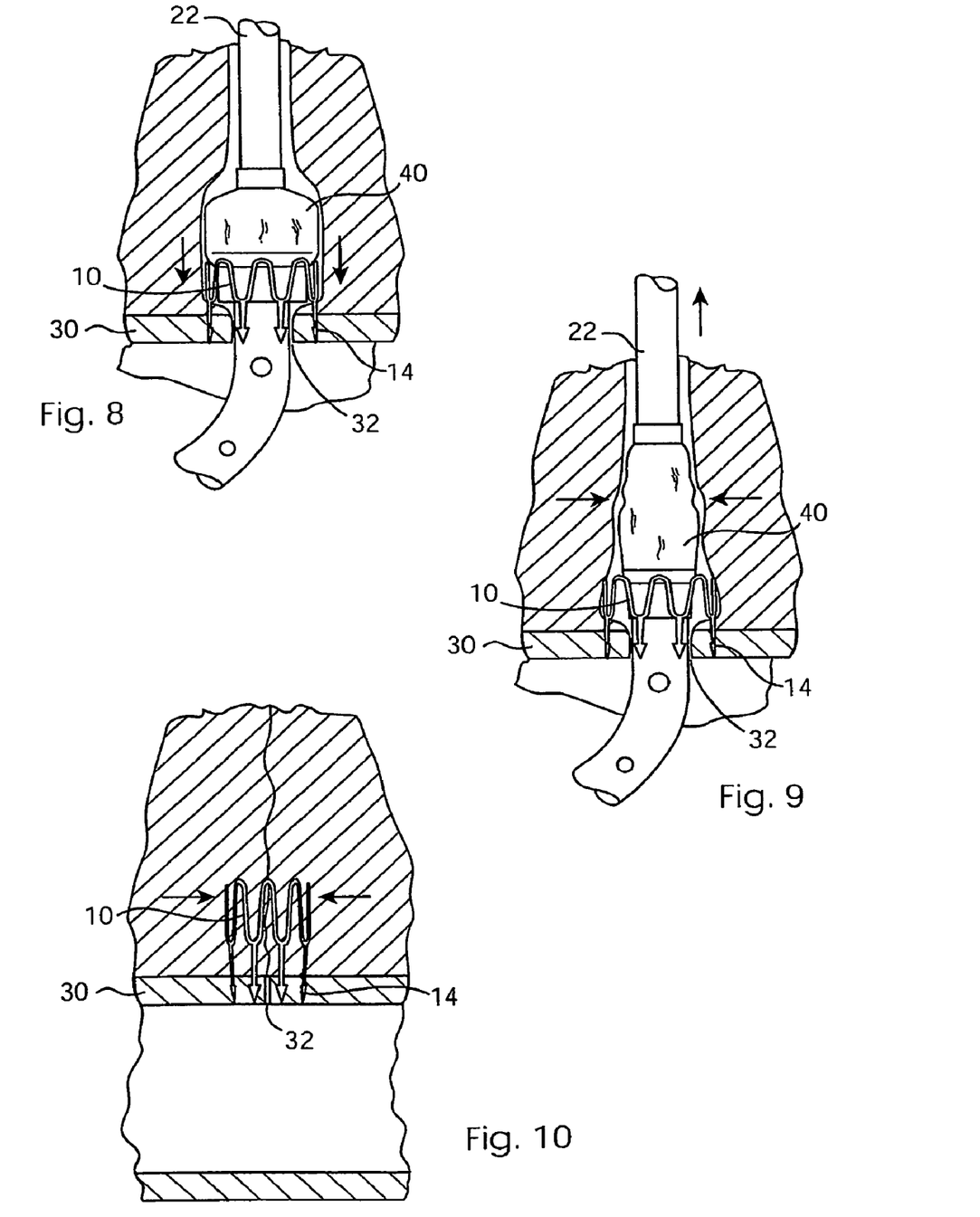

FIGS. 6 to 10 illustrate the device in clinical use. Referring first to FIG. 6, the catheter 22 is positioned on the guide wire 26 and slid forwardly thereon through the tissue tract until the front end 28 of the catheter enters the blood vessel 30. The catheter 22 is advanced forward until the blood entry port 34 enters the blood vessel indicated by blood flowing from the bleed back port 44. Advancement of the catheter is stopped and the balloon 40 is then inflated, as illustrated in FIG. 7, by fluid pressure applied at the port 46. Inflation of the balloon causes the ring occluder 10 to resiliently expand. Once fully expanded the catheter 22 is advanced forwardly as shown in FIG. 8. In doing so, the shoulder 40c on the balloon 40 pushes against the ring occluder 10 causing the prongs 14 to penetrating overlying tissue and the arterial wall. The catheter 22 is advanced until significant resistance prevents any further advancement. This indicates proper position of the ring occluder 10. Now the balloon 40 is fully deflated by venting through the port 46 resulting in some resilient contraction of the ring occluder 10 around the catheter 22 as illustrated in FIG. 9. Once fully deflated the guide wire 26 and catheter 22 are removed from the tissue tract and the puncture hole 32 causing the ring occluder 10 to resiliently contract to its initial state thereby pulling the edges of the puncture hole 32 together and effecting homeostasis. The closed ring occluder 10 remains positioned around the puncture hole on the artery as illustrated in FIG. 10.

Although the foregoing has shown the ring 12 or 12' as circular, and the balloon 40 circularly symmetric around the catheter 22, the ring does not need to be circular but can be any closed-loop shape as dictated by the cross-section of the balloon which can also vary. The term "ring" is to be interpreted accordingly.

Figure 11:
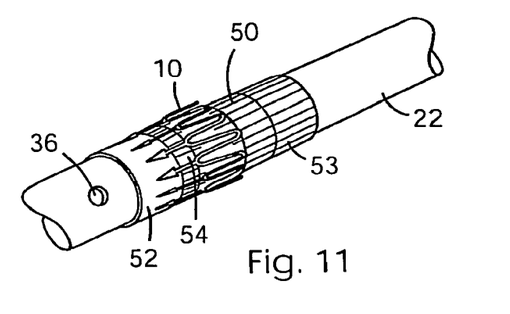
FIG. 11 is a perspective view of a second embodiment of catheter delivery device in a non-expanded condition.
Figure 11A:
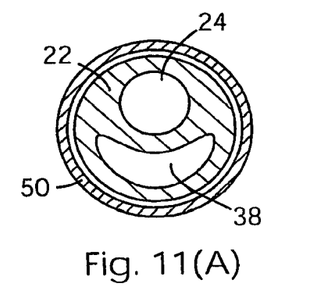
FIG. 11(A) is a cross sectional view of the second embodiment of catheter on the plane A-A of FIG. 12.
Figure 12:
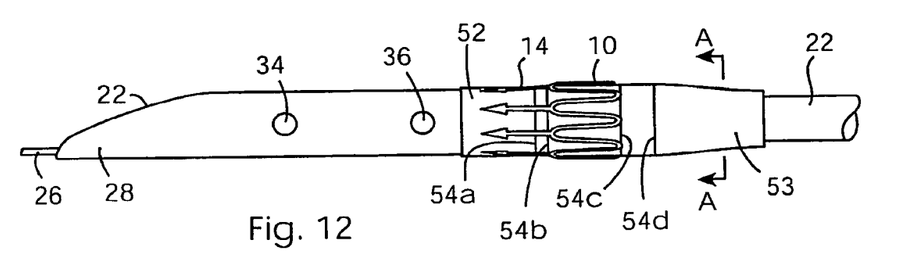
FIG. 12 is an elevational view of the device shown in FIG. 11.
Figure 13:
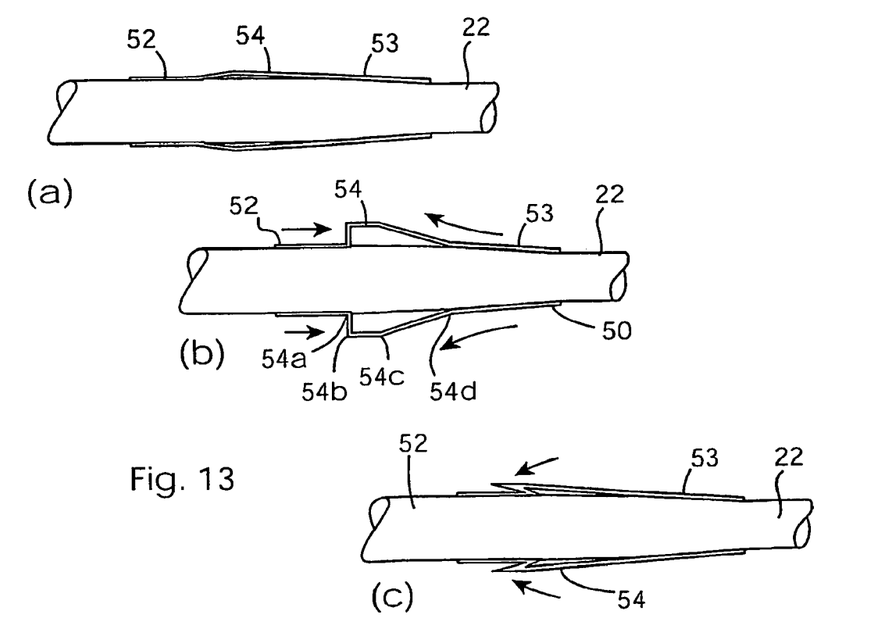
FIG. 13(A) is an elevational view of the ring occluder deployment means (expander) of the second embodiment of catheter delivery device in its initial rest position.
FIG. 13(B) is an elevational view of the expander of FIG. 13(A) in its mid-forward and fully expanded state.
FIG. 13(C) is an elevational view of the expander of FIG. 13(A) in its fully forward and collapsed state.

FIGS. 11 to 13 show an alternative embodiment of a catheter delivery device for the ring occluder 10 or 10'. In place of the balloon 40 used in the previous embodiment, a mechanical expander is used; otherwise, all features of the previous embodiment may be present in the current embodiment. The mechanical expander comprises an oversleeve 50 on the catheter 22. FIG. 11(A) shows a cross-section through the catheter in the region of the oversleeve 50. The catheter has a longitudinal guide wire bore 24 and blood return bore 38 as previously described, and the sleeve 50 is seen coaxially surrounding the catheter body. The forward end 52 of the sleeve is fixed to the outer surface of the catheter, while the rear end 53 of the sleeve 50 is slidable on the catheter 22. A section of the sleeve 50 intermediate its ends, onto which the occluder is mounted in use, is slit longitudinally to form a series of spines 54. Each spline 54 has four hinge points 54a, 54b, 54c and 54d, the hinge points 54a and 54d being at the front and rear ends of the spline and the hinge points 54b and 54c being intermediate them. The two intermediate hinge points 54b, 54c generally align with the upper and lower edges respectively of the expandable ring 12 section of the occluder 10 as illustrated in FIG. 12.

In the unexpanded state as shown in FIG. 13(a) the splines 54 lie flush with the catheter. If the rear end 53 of the sleeve 50 is slid along the catheter 22 towards the fixed front end 52 the splines 54 are forced mutually radially outwardly as shown in FIG. 13(b) thus resiliently expanding the occluder 10 and at the same time advancing it in a forward direction. With continued advancement of the rear end 53 of the sleeve the splines collapse mutually inwardly down onto the catheter thus releasing the occluder 10 from the splined section.

Figure 14:
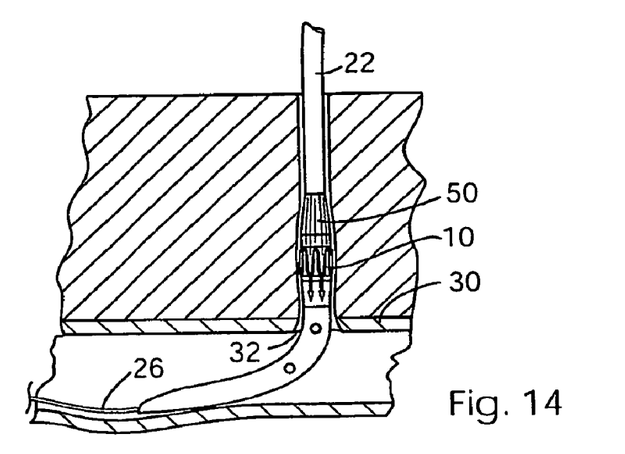
FIGS. 14 and 15 illustrate successive stages of the second embodiment of catheter delivery device in use.
Figure 15:
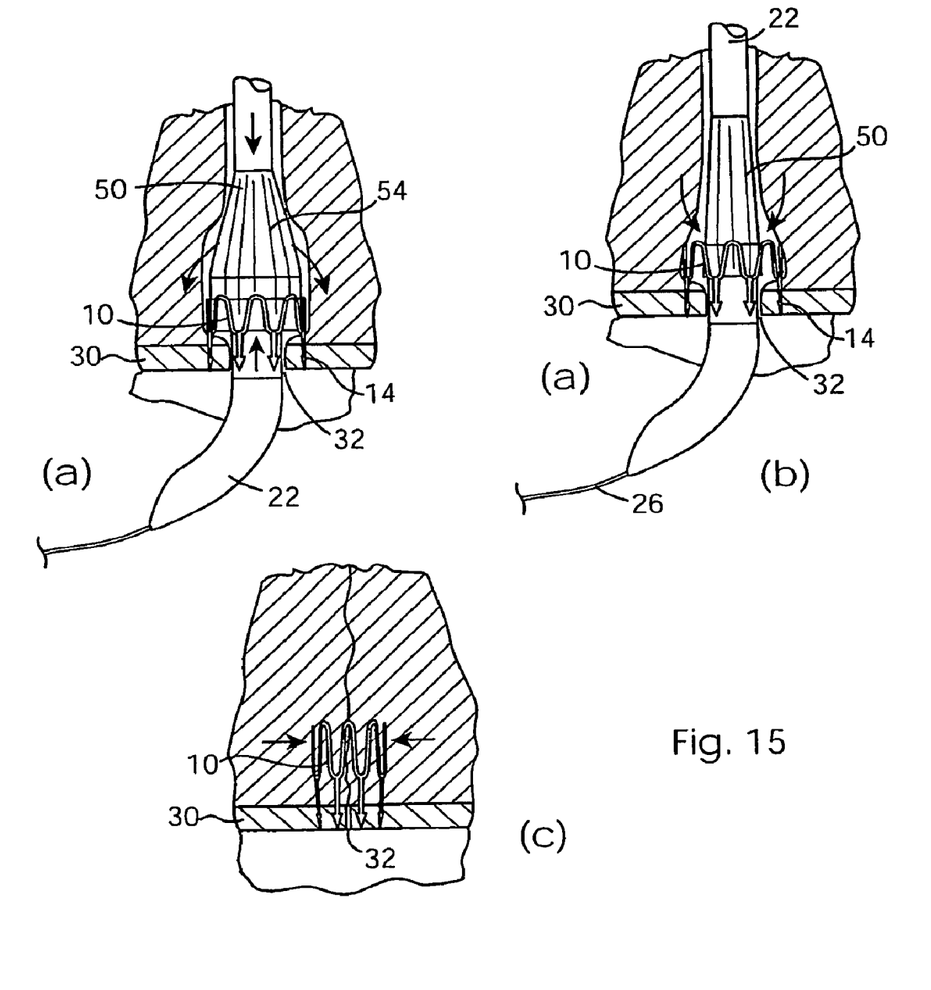

In clinical use, the catheter 22 is slid over a guide wire 26 as shown in FIG. 14 until a blood signal is received at the port 44 thus indicating proper positioning. At this point, the rear end 53 of the sleeve 50 is advanced causing the occluder 10 to resiliently expand and simultaneously advance to stab the wall 30 of the artery, FIG. 15(a). As the rear end 53 of the sleeve is advanced further it releases the occluder 10, FIG. 15(b), so that the catheter and guide wire can be retracted from the puncture hole 32 allowing the occluder 10 to fully contract and close the puncture hole, FIG. 15(c).

The invention is not limited to the embodiments described herein which may be modified or varied without departing from the scope of the invention.

The invention claimed is:

1. A method for closing a puncture in a body lumen, the method comprising:
    advancing a catheter until an indication that the catheter is positioned within a body lumen;
    increasing a dimension of a clip expander to increase a dimension of a clip, the clip having a ring disposed around the clip expander and prongs projecting towards the front end of the catheter;
    advancing the catheter to cause the clip to penetrate tissue surrounding the wall of the body lumen;
    decreasing a dimension of the clip expander; and
    removing the catheter from the tissue tract causing the clip to pull the surrounding tissue together substantially sealing the puncture.

2. The method of claim 1, wherein the clip expander further comprises a balloon.

3. The method of claim 2, wherein the balloon includes a shoulder to advance the clip toward a distal end of the catheter.

4. The method of claim 1, wherein the clip expander further comprises a sliding collar.

5. The method of claim 4, wherein the sliding collar further comprises splines.

6. The method of claim 5, further comprising forcing the splines mutually outwards to deform the clip.

7. The method of claim 1, wherein the indication that the catheter is positioned within a body lumen further comprises an indication of blood in a bleed back indicator.

8. The method of claim 1, wherein the increasing a dimension of the clip expander increases a dimension of the ring of the clip.

9. The method of claim 1, wherein advancing the catheter to cause the clip to penetrate tissue surrounding the wall of the body lumen is performed after increasing the dimension of the clip expander to increase a dimension of the clip.

10. The method of claim 9, wherein decreasing the dimension of the clip expander is performed after advancing the catheter to cause the clip to penetrate tissue surrounding the wall of the body lumen.

11. A method for closing a puncture in a body lumen, the method comprising:
   advancing a catheter until an indication that a clip is positioned a pre-determined distance from a wall of the body lumen;
   increasing a dimension of a clip expander to increase a dimension of the clip;
   advancing the catheter to cause the clip to penetrate tissue surrounding the wall of the body lumen;
   decreasing a dimension of the clip expander; and
   removing the catheter from the tissue tract causing the clip to pull the surrounding tissue together substantially sealing the puncture.

12. A method for closing a puncture in a body lumen, the method comprising:
   advancing a catheter until an indication that a clip is positioned a pre-determined distance from a wall of the body lumen;
   after advancing the catheter until the indication that the clip is positioned, increasing a dimension of a clip expander to increase a dimension of the clip, the clip expander comprising a sleeve surrounding the body which has one end fixed relative to the body, a section of the sleeve intermediate its ends being slit longitudinally to form a plurality of splines which can be forced mutually outwardly by sliding the other end of the sleeve along the body towards the fixed end of the sleeve, the clip having a ring disposed around the expander and prongs projecting towards the front end of the body, the clip being mounted on the splined section of the sleeve;
   while increasing the dimension of the clip expander, advancing the catheter to cause the clip to penetrate tissue surrounding the wall of the body lumen;
   after advancing the catheter to cause the clip to penetrate tissue, decreasing a dimension of the clip expander; and
   removing the catheter from the tissue tract causing the clip to pull the surrounding tissue together substantially sealing the puncture.

* * * * *